United States Patent
Petsch

(10) Patent No.: US 9,351,901 B1
(45) Date of Patent: May 31, 2016

(54) GAIT TRAINING TOOL

(71) Applicant: Cassi Lee Petsch, Austin, TX (US)

(72) Inventor: Cassi Lee Petsch, Austin, TX (US)

( * ) Notice: Subject to any disclaimer, the term of this patent is extended or adjusted under 35 U.S.C. 154(b) by 15 days.

(21) Appl. No.: 14/566,538

(22) Filed: Dec. 10, 2014

Related U.S. Application Data

(60) Provisional application No. 61/950,665, filed on Mar. 10, 2014, provisional application No. 61/919,787, filed on Dec. 22, 2013, provisional application No. 61/914,906, filed on Dec. 11, 2013.

(51) Int. Cl.
*A63B 22/00* (2006.01)
*A61H 3/00* (2006.01)

(52) U.S. Cl.
CPC ............... *A61H 3/00* (2013.01); *A63B 22/001* (2013.01); *A61H 2003/007* (2013.01)

(58) Field of Classification Search
USPC .................................................... 482/1–148
See application file for complete search history.

(56) References Cited

U.S. PATENT DOCUMENTS

| | | | | |
|---|---|---|---|---|
| 2,556,121 A * | 6/1951 | Thomas | ........... | A61G 5/10 280/304.1 |
| 2,596,055 A * | 5/1952 | Thomas | ........... | A61G 5/14 280/304.1 |
| 2,897,616 A * | 8/1959 | Edwards | ........... | H02G 11/003 248/240.4 |
| 3,398,974 A | 8/1968 | Edwards | | |
| 3,708,182 A | 1/1973 | Markiel | | |
| 3,759,544 A | 9/1973 | Korpela | | |
| 3,999,778 A | 12/1976 | Markiel | | |
| 4,368,898 A | 1/1983 | Lay | | |
| 4,441,710 A * | 4/1984 | Lay | ........... | A61G 5/00 473/56 |
| 4,491,257 A * | 1/1985 | Ingles | ........... | A61H 3/00 135/66 |
| 4,530,522 A * | 7/1985 | Walker | ........... | F16L 25/00 285/368 |
| 4,809,804 A | 3/1989 | Houston | | |
| 4,997,154 A * | 3/1991 | Little | ........... | A61G 5/08 248/230.5 |
| 5,076,390 A | 12/1991 | Haskins | | |
| 5,419,571 A * | 5/1995 | Vaughan | ........... | A61G 5/10 280/250.1 |
| 5,451,193 A | 9/1995 | Pickard | | |
| 5,516,021 A * | 5/1996 | Douglass | ........... | A61G 5/10 224/407 |
| 5,556,299 A * | 9/1996 | Finke | ........... | H01R 11/15 439/479 |
| 5,779,118 A * | 7/1998 | Douglass | ........... | A61G 5/10 224/407 |
| 5,820,152 A | 10/1998 | Warren-Pfaeffle | | |
| 5,901,891 A * | 5/1999 | Douglass | ........... | A61G 5/10 135/66 |
| 6,058,888 A * | 5/2000 | Nichols | ........... | A01K 15/027 119/702 |
| 6,378,539 B1 * | 4/2002 | Allee | ........... | A45B 11/00 135/16 |
| 6,893,012 B2 * | 5/2005 | Wong | ........... | B25B 5/006 269/182 |
| 6,930,603 B2 * | 8/2005 | Jackson | ........... | G08B 21/22 135/65 |
| 6,966,470 B1 * | 11/2005 | Charlton | ........... | A45C 13/26 135/66 |
| 7,422,550 B1 | 9/2008 | Pinero | | |

(Continued)

FOREIGN PATENT DOCUMENTS

| | | |
|---|---|---|
| GB | 2178375 | 2/1987 |
| TW | M442147 | 12/2012 |

*Primary Examiner* — Stephen Crow

(74) *Attorney, Agent, or Firm* — Eric Karich; Karich & Associates

(57) ABSTRACT

A gait training tool has an elongate frame structure having a proximal end and a distal end, with a wheelchair clamp attached to the proximal end. The tool further includes a walker connection attachment, and a manual gripping attachment, which can be interchangeably mounted on the distal end of the elongate frame structure for performing different forms of gait training. The walker connection attachment has a walker clamp for attachment to a walker. The manual gripping attachment has a cylindrical gripping structure that is adapted for manually gripping and pulling the elongate frame structure.

12 Claims, 6 Drawing Sheets

(56) References Cited

U.S. PATENT DOCUMENTS

| | | | | |
|---|---|---|---|---|
| 7,699,276 B2 * | 4/2010 | Melic | | E04G 21/3233 |
| | | | | 248/200.1 |
| 7,963,294 B1 * | 6/2011 | Trout | | A61H 3/00 |
| | | | | 135/66 |
| 8,012,070 B2 * | 9/2011 | James | | A63B 21/00069 |
| | | | | 482/114 |
| 8,162,346 B2 | 4/2012 | Purdue | | |
| 8,360,518 B2 | 1/2013 | Braaten | | |
| 8,608,038 B2 * | 12/2013 | Katchen | | A61G 5/10 |
| | | | | 224/275 |
| 8,702,567 B2 * | 4/2014 | Hu | | A61H 3/00 |
| | | | | 482/8 |
| 9,107,481 B2 * | 8/2015 | Catchings | | A45B 3/00 |
| 9,180,063 B2 * | 11/2015 | Friedman | | G08C 19/00 |
| 2006/0028544 A1 * | 2/2006 | Tseng | | A61H 3/061 |
| | | | | 348/62 |
| 2006/0100546 A1 * | 5/2006 | Silk | | A61B 5/1038 |
| | | | | 600/592 |
| 2006/0292533 A1 * | 12/2006 | Selod | | A63B 71/0686 |
| | | | | 434/247 |
| 2008/0246246 A1 * | 10/2008 | Dix | | A61G 5/023 |
| | | | | 280/233 |
| 2009/0060473 A1 * | 3/2009 | Kohte | | F16H 11/041 |
| | | | | 386/200 |
| 2009/0145470 A1 * | 6/2009 | Couper | | A45B 1/04 |
| | | | | 135/66 |
| 2009/0170672 A1 * | 7/2009 | McMullen | | A63B 21/0552 |
| | | | | 482/129 |
| 2010/0204018 A1 * | 8/2010 | Hoggan | | A63B 22/0012 |
| | | | | 482/54 |
| 2012/0174314 A1 | 7/2012 | Clement | | |
| 2012/0232442 A1 | 9/2012 | Wang | | |
| 2013/0106077 A1 | 5/2013 | Nagel | | |
| 2013/0274640 A1 | 10/2013 | Butters | | |
| 2013/0306119 A1 * | 11/2013 | Catchings | | A45B 3/00 |
| | | | | 135/66 |
| 2014/0276266 A1 * | 9/2014 | Kim | | A63B 69/0064 |
| | | | | 601/35 |
| 2015/0342822 A1 * | 12/2015 | Osterhaus | | A61H 3/04 |
| | | | | 280/657 |

\* cited by examiner

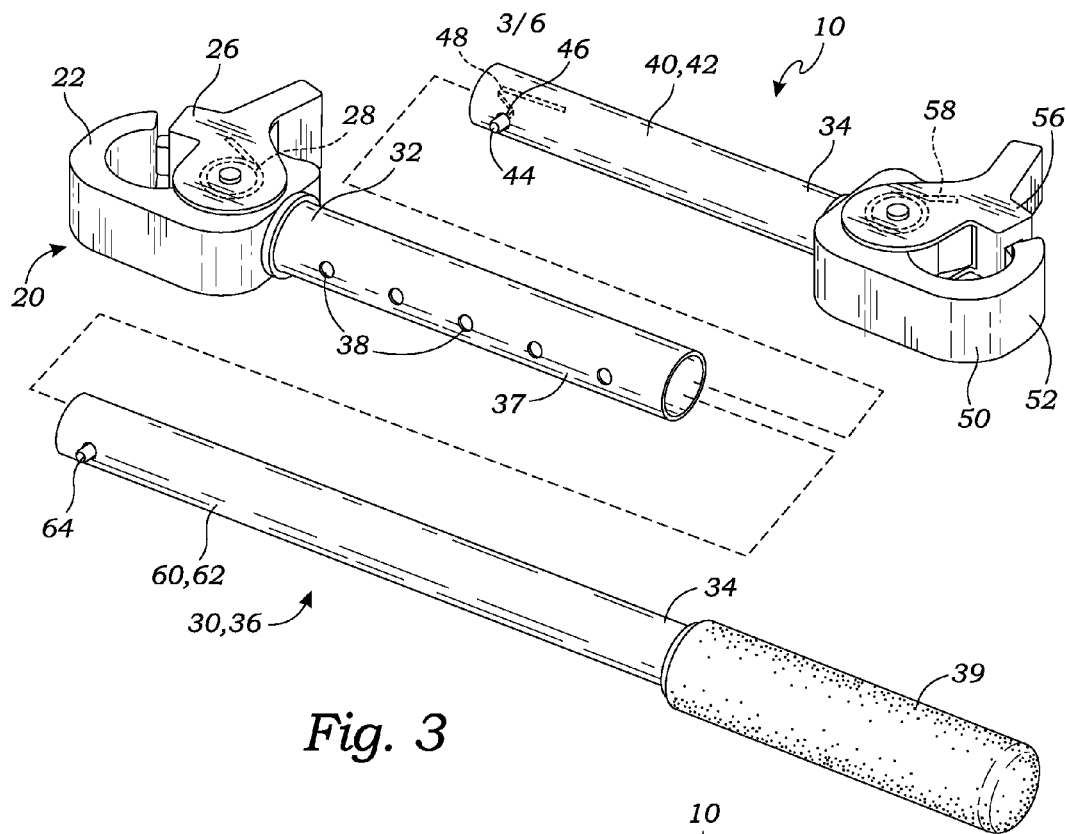
Fig. 3
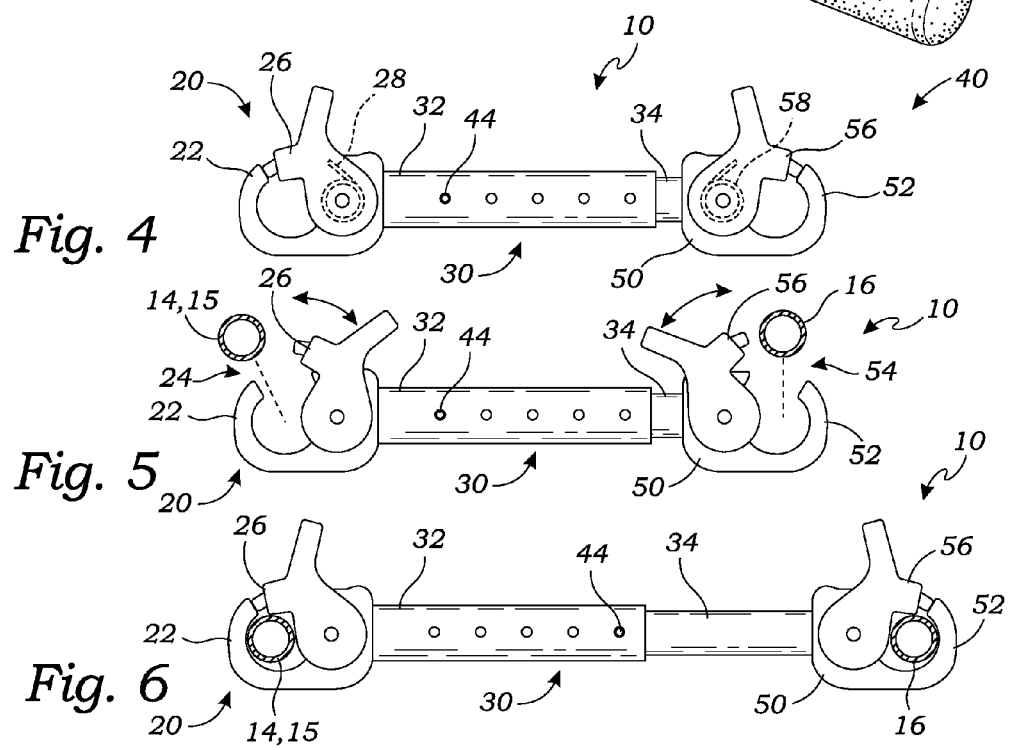
Fig. 4
Fig. 5
Fig. 6

GAIT TRAINING TOOL

CROSS-REFERENCE TO RELATED APPLICATIONS

This application for a utility patent claims the benefit of the following U.S. Provisional Applications: application 61/950,665, filed Mar. 10, 2014; application 61/919,787, filed Dec. 22, 2013; and application 61/914,906, filed Dec. 11, 2013.

STATEMENT REGARDING FEDERALLY SPONSORED RESEARCH

This invention was supported by NIH R24HDO65703 from the National Center for Medical Rehabilitation Research in the Eunice Kennedy Shriver National Institute of Child Health & Human Development at the National Institutes of Health and the Center for Translation of Rehabilitation Engineering Advances and Technology (TREAT).

BACKGROUND OF THE INVENTION

1. Field of the Invention

This invention relates generally to tools for assisting patients with gait training, and more particularly to a gait training tool that may be removably attached to a wheelchair for enabling an improved method of gait/ambulation/walking training and/or assistance.

2. Description of Related Art

The present invention is a gait training tool adapted for assisting patients with walking using an assistive device. More specifically, the invention is used by a rehabilitation specialist, healthcare professional, gait analysis professional, restorative person/technician, aide, caretaker, or similar person (hereinafter to be referred to as "caregiver") who provide gait/ambulation/walking training and/or assistance (hereinafter to be referred to as "gait training"). The device is used with a wheelchair, and may also be used in conjunction with a standard four-legged walker, front wheeled walker, four wheeled walker, medical walker, or similar assistive device (hereinafter to be referred to as "walker"). The invention is particularly used for patients with a gait abnormality, compromised gait pattern, medical ailment, ataxia, or similar problem, or who require increased physical assistance and/or frequent rest breaks.

Currently, gait training involves using a gait belt around the patient's waist while the staff member holds the gait belt with one hand to ensure patient safety in the event of a fall, loss of balance, knee buckling or other unfortunate event. Full attention must be given to the patient and if attention must be diverted, gait training is stopped. Signs of fatigue from the patient must be immediately observed by the staff member and the patient must be allowed to rest when needed. To ensure the patient can rest when required or if an unfortunate event occurs, the staff member must pull/guide a wheelchair behind the patient.

There are a number of complications for both the staff member and patient when using a gait belt. This gait procedure causes the staff member to be behind the patient with one hand on the gait belt and the other hand pulling the wheelchair. With the staff member behind the patient, the staff member cannot provide adequate eye-contact, assistance, visual demonstration, support, guidance and communication which is optimally beneficial to patient instruction and carryover. Also, the staff member is unable to proficiently execute the three ideal learning styles for the patient's optimal comprehension; kinesthetic, visual, and auditory.

Many patients confined to wheelchairs after surgery, strokes, accidents, joint replacements and so forth are required to undergo physical therapy to learn to stand and walk again. Ideally, this requires one caregiver to assist the patient with standing and walking and a second caregiver the push a wheelchair behind the patient in case the patient needs to sit down. This is costly due to the fact that two caregivers are needed to assist the patient.

If a second caregiver is not available, then the first caregiver must keep one hand on the patient and the other hand on the wheelchair or drag the wheelchair with his or her foot behind the patient, thus creating a dangerous situation because the caregiver does not have a solid hold on the patient.

Therefore, a need exists for a device that will allow a caregiver to pull a wheelchair behind the patient while still maintaining a solid hold on the patient, thereby eliminating the need for the second caregiver to push the wheelchair behind the patient.

Nagel, U.S. 2013/0106077, teaches a wheelchair pull strap that is attached to both the wheelchair and the caregiver, so that as the caregiver walks with the patent, he or she pulls the wheelchair along with him or her. The disadvantage of this type of strap is that the pull strap can interfere with the caregiver's use of his or her hands, and also interfere with the patient sitting in the wheelchair.

The prior art also teaches a walker that can be attached to the wheelchair, for dragging the wheelchair behind the patient. Thomas, U.S. Pat. No. 2,556,121, teaches a detachable wheelchair walking apparatus that functions as a walker, and which can be attached to a wheelchair so that the walker drags the wheelchair along with the patient. While the Thomas apparatus is functional, it includes an entire walker, and is therefore large, cumbersome, and expensive.

The prior art teaches various devices for pulling a wheelchair during physical therapy. However, the prior art does not teach a simple and easy to use device that can be attached to a standard wheelchair and, optionally, to a walker, for enabling the caregiver to control the wheelchair while attending to the patient during physical therapy. The present invention fulfills these needs and provides further advantages as described in the following summary.

SUMMARY OF THE INVENTION

The present invention teaches certain benefits in construction and use which give rise to the objectives described below.

The present invention provides a gait training tool for performing assisted gait training of a patient using a wheelchair having a frame. The gait training tool comprises an elongate frame structure having a proximal end and a distal end; a wheelchair clamp attached to the proximal end of the elongate frame structure; a walker connection attachment having a walker clamp and an engaging structure for removably engaging the walker connection attachment on the distal end of the elongate frame structure; and a manual gripping attachment having a cylindrical gripping structure and an engaging structure for removably engaging the manual gripping attachment on the distal end of the elongate frame structure.

The present invention is an adjustable length apparatus that can be manually pulled by a caregiver, or, optionally, to attach the wheelchair directly to the walker and enable the wheelchair to follow behind the patient as they ambulate. The device is an adjustable length rod with a clamp for attachment to a wheelchair, and, optionally, a second clamp to attach the wheelchair to the walker. With the present invention, the staff member will no longer be required to use one of his/her hands to pull the wheelchair behind the patient, allowing the staff member to have both hands on the patient, improving overall efficiency of gait instruction and proper body mechanics.

The unique construction of the present invention enables the caregiver to position themselves adjacent to the patient, in front of the patient or at his or her side, increasing their line of sight instruction and ensuring the effectiveness of instruction. Adjacent positioning also enables the caregiver to be alongside the patient, improving hands on capabilities and safety of the patient during ambulation in case of a fall or loss of balance.

The device also promotes ergonomically correct body mechanics for the caregiver during ambulation, thereby reducing fatigue, stress, and risk of injury to the caregiver.

The present invention also allows the wheelchair to be optimally positioned behind the patient by adjusting the length of the rod to accommodate the patient's body frame, size and specific needs. Ideal following distance of the wheelchair would be based on the patient's specific medical condition, acuity, strength, and activity tolerance. Lower level functioning patients would require a very immediate wheelchair follow, while a higher level patient would tolerate a larger margin, both of which can be achieved through the lengthening capabilities of this device.

The device is able to be attached to either the right or left side of the corresponding arm support/frame of the wheelchair and posterior leg of the walker, dependent upon patient's needs.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 3 is an exploded perspective view of a third embodiment of the gait training tool, illustrating two different attachments, a walker connection attachment, and a manual gripping attachment;

FIG. 4 is a top plan view of the gait training tool of FIG. 3, illustrating the walker connection attachment in a shortened configuration with locking arms of a wheelchair clamp and a walker clamp closed;

FIG. 5 is a top plan view of the gait training tool of FIG. 3, illustrating the locking arms of the clamps open for receiving the frame of the wheelchair and the walker;

FIG. 6 is a top plan view of the gait training tool of FIG. 3, illustrating the gait training tool in a lengthened configuration with the locking arms of the clamps closed around the frame of the wheelchair and the walker;

DETAILED DESCRIPTION OF THE INVENTION

The above-described drawing figures illustrate the invention, a gait training tool 10 that enables a unique method of performing assisted gait training of a patient 12 using a wheelchair 14. For purposes of this application, the term "gait training" is defined to include gait training, ambulation, walking training or assistance, and any other similar training, rehabilitation, or related exercises, training, or treatment.

Figure 1:
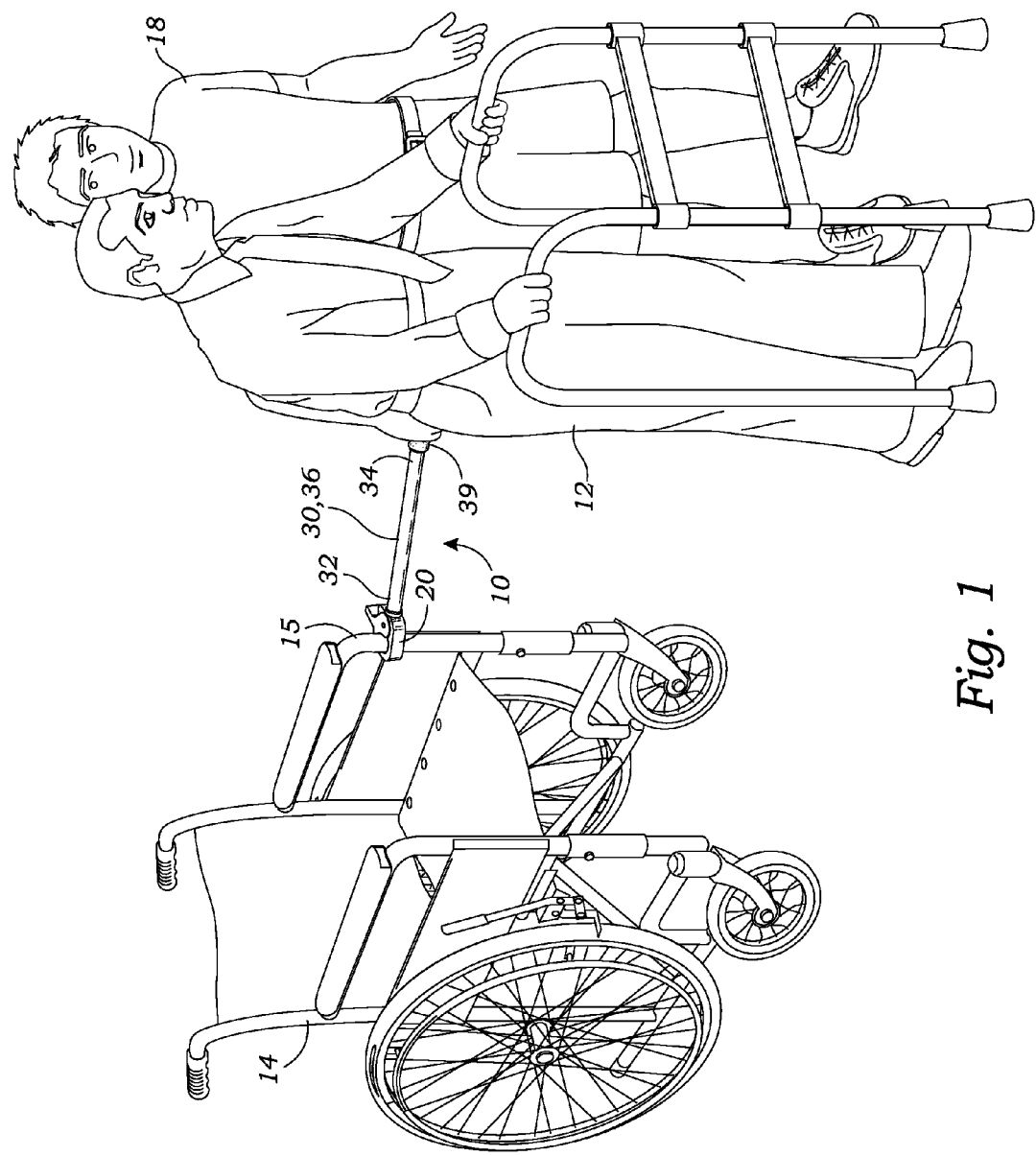
FIG. 1 is a perspective view of one embodiment of a gait training tool operatively attached to a frame of a wheelchair and manually pulled by the caregiver during assisted gait training.

FIG. 1 is a perspective view of one embodiment of a gait training tool 10 operatively attached to a frame 15 of the wheelchair 14 and manually pulled by a caregiver 18 during the assisted gait training. As shown in FIG. 1, the gait training tool 10 comprises a wheelchair clamp 20 and an elongate frame structure 30.

The wheelchair clamp 20 is sized and shaped to removably clamp a frame 15 of the wheelchair 14. Any form of clamp, hitch, removable connection, or other mechanism for removably attaching the gait training tool 10 to the wheelchair 14 may be used, and one particular embodiment is discussed in greater detail below. Those skilled in the art may devise alternative structures for removably attaching the gait training tool 10 to the wheelchair 14, and such alternatives should be considered within the scope of the present invention.

The elongate frame structure 30 extends from the wheelchair clamp 20, and includes a proximal end 32 adjacent to the wheelchair clamp 20, and a distal end 34 opposite the proximal end 32. The elongate frame structure 30 is adapted to enable a caregiver 18 to pull the wheelchair 14 while standing adjacent to the patient 12. In this embodiment, the elongate frame structure 30 is about 12-36 inches in length, preferably about 12-24 inches in length, although alternative lengths may be used if deemed suitable by one skilled in the art. For purposes of this application, the term "about" is defined to mean +/−10%.

In this embodiment, the distal end 34 of the elongate frame structure 30 includes a cylindrical gripping structure 39 suitable for gripping by a human hand. In this embodiment, the cylindrical gripping structure 39 is constructed of a foam rubber sleeve which has a round cross-sectional shape, and is mounted (e.g., bonded) onto the distal end 34 of the elongate frame structure 30. For purposes of this application, the term "foam rubber" is hereby defined to include any form of rubber or rubber-like material, including but not limited to polyurethane, latex, or similar material, manufactured with a foaming agent to create an air filled matrix structure. In alternative embodiments, the elongate frame structure 30 may be wrapped with a tape of other material, having a tacky, easily gripped texture and feel. The cylindrical gripping structure 39 may also have alternative cross-sectional shapes, and/or be constructed in other manners known in the art that are suitable for easy gripping by the caregiver 18.

In use, the wheelchair clamp 20 is attached to the frame 15 of the wheelchair 14 so that the elongate frame structure 30 extends in front of the wheelchair 14. The patient 12 is then positioned in front of the wheelchair 14 facing away from the wheelchair 14, and the caregiver 18 stands adjacent to the patient 12, facing the patient 12, in a position to assist the patient 12 with gait training. As the patient 12 walks forward, the caregiver 18 (or the patient himself or herself, if desired)

is able to pull the wheelchair 14 via the gait training tool 10 as the patient 12 walks forward during the gait training. The caregiver 18 is able to face the patient 12 ready to render assistance if needed, while the wheelchair 14 remains close behind the patient 12 during the gait training.

Figure 2:
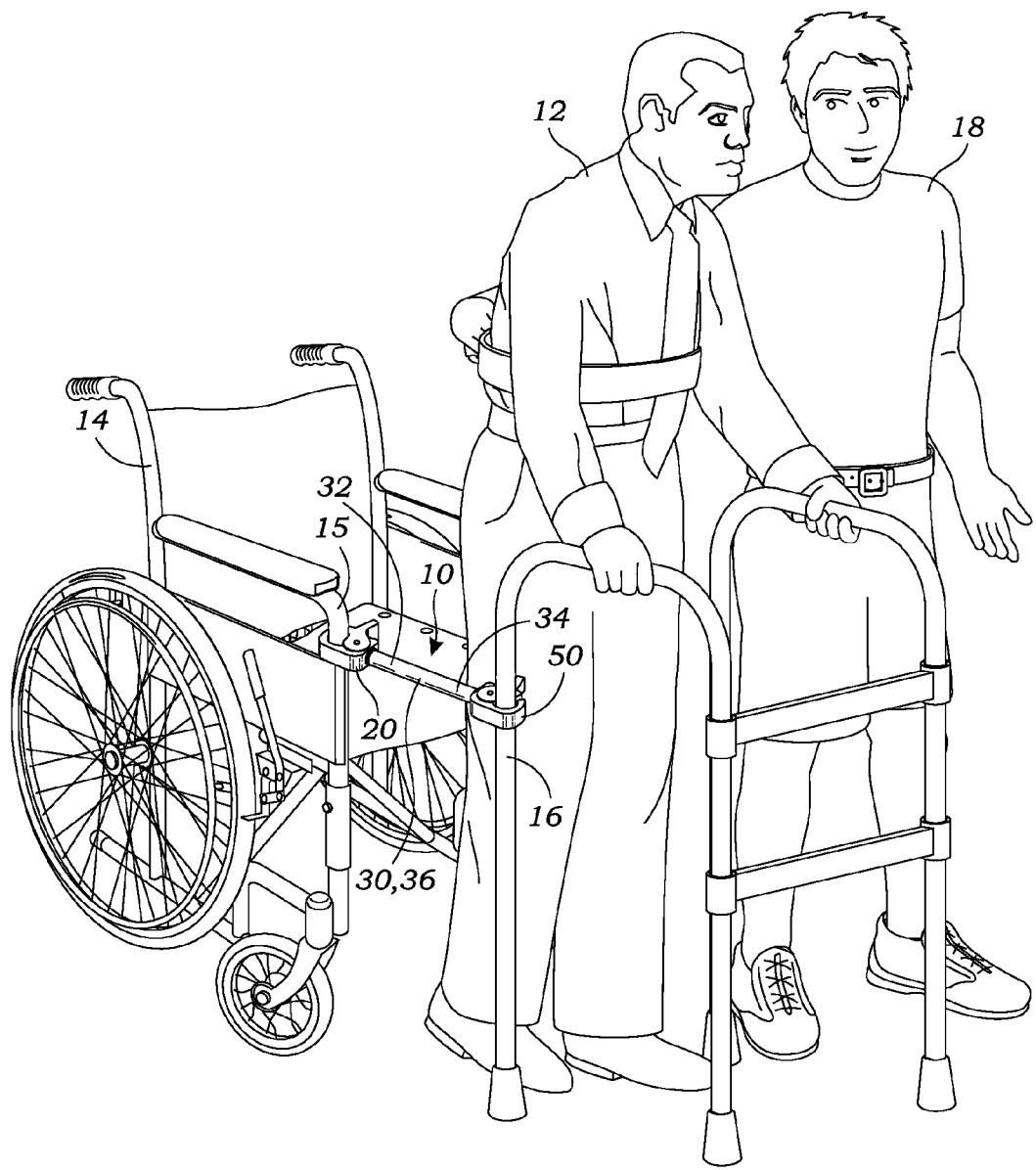
FIG. 2 is a perspective view of a second embodiment of the gait training tool operatively attached to the wheelchair and also to a walker while a caregiver performs assisted gait training.

FIG. 2 is a perspective view of a second embodiment of the gait training tool 10 operatively attached to the wheelchair 14 and also to a walker 16 while the caregiver 18 performs the assisted gait training. In this embodiment, the gait training tool 10 further includes a walker clamp 50 at the distal end 34 of the elongate frame structure 30. The walker clamp 50 is sized and shaped to removably clamp the walker 16. While one embodiment of the walker clamp 50 is shown, as discussed in greater detail below, any form of clamp, hitch, removable connection, or other mechanism for removably attaching the gait training tool 10 to the walker 16 may be used. Those skilled in the art may devise alternative structures for removably attaching the gait training tool 10 to the walker 16, and such alternatives should be considered within the scope of the present invention.

In this embodiment, the distal end 34 of the elongate frame structure 30 is attached to the walker 16 (e.g., with the walker clamp 50). The gait training is performed substantially as described above, only the gait training tool 10 pulls the wheelchair 14 as the walker 16 is moved forward. The walker 16 is progressed along with the patient 12 during forward movement, either by the patient 12 or by the caregiver 18 if the patient 12 is unable to do so, and the forward movement of the walker 16 pulls the wheelchair 14 behind the patient 12 via the gait training tool 10.

FIG. 3 is an exploded perspective view of a third embodiment of the gait training tool 10, illustrating two different attachments, a walker connection attachment 40, and a manual gripping attachment 60. The walker connection attachment 40 includes a walker clamp 50 for clamping the walker 16, as discussed above and as shown in FIG. 2. The manual gripping attachment 60 includes a cylindrical gripping structure 39 for manually pulling the gait training tool 10, as discussed above and as shown in FIG. 1. Both of these attachments 40 and 60 are discussed in greater detail below.

In the embodiment of FIG. 3, the elongate frame structure 30 includes two different components, a first frame element 36 and a second frame element 42, that slidably engage each other so that the overall length of the elongate frame structure 30 is adjustable. In the embodiment of FIG. 3, the first frame element 36 and the second frame element 42 are both elongate tubular structures, and they telescopically engage each other. In alternative embodiments, one or both of the elements 36 or 42 may be in another form; for example, one of the elements 36 or 42 may be in the form of a collar or similar structure for sliding up and down the other of the elements 36 or 42. Alternative structures that may be devised by one skilled in the art are considered within the scope of the present invention, and should be considered within the scope of the claimed invention.

In this embodiment, the elongate frame structure 30 further including a locking element 44 that interlocks the first and second frame elements 36 and 42 so that they are locked in place with respect to one another.

In this embodiment, the locking element 44 is a locking pin that fits through an aperture 46 of the second frame element 42, biased outwardly by a spring 48, to engage one of a plurality of apertures 38 through the first frame element 36. While one version of the locking element 44 is shown in FIG. 3, those skilled in the art can devise alternative locking mechanisms, and such alternatives and equivalents should be considered within the scope of the present invention. Furthermore, the locking pin 44, the aperture 46, and plurality of apertures 38 are all expressly defined to include the inverse construction, wherein the locking pin 44 and the plurality of apertures 38 are reversed.

The method of use includes the steps of adjusting the first and second frame elements 36 and 42 with respect to each other so that the elongate frame structure 30 is a selected length, and then locking the elongate frame structure 30 with the locking structure 44. In this embodiment, the first and second frame elements 36 and 42 are adjusted, and the locking pin 44 is positioned through one of the plurality of apertures 38 to lock the first and second frame elements 36 and 42 in the selected configuration.

FIG. 4 is a top plan view of the gait training tool 10 of FIG. 3, illustrating the walker connection attachment 40 in a shortened configuration with locking arms 26 and 56 of the wheelchair clamp 20 and the walker clamp 50 closed. FIG. 5 is a top plan view thereof illustrating the locking arms 26 and 56 open for receiving the frame 15 of the wheelchair 14, and the walker 16. FIG. 6 is a top plan view thereof illustrating the gait training tool 10 in a lengthened configuration with the locking arms 26 and 56 closed around the frame 15 of the wheelchair 14, and the walker 16.

As shown in FIGS. 3-6, in the present embodiment, the wheelchair clamp 20 includes a C-shaped hook body 22 that is shaped to fit around the frame 15 of the wheelchair 14, the C-shaped hook body 22 defining an opening 24 sized to receive the frame 15 of the wheelchair 14 therethrough. The C-shaped hook body 22 may further include a locking arm 26 that is pivotally connected to the C-shaped hook body 22 for closing the opening 24 of the C-shaped hook body 22, and a biasing spring 28 for biasing the locking arm 26 from an open position wherein the opening 24 is open, to a closed position wherein the opening 24 is closed.

The walker clamp 50 may be of essentially identical construction, and similarly include a C-shaped hook body 52 that is shaped to fit around the walker 16, the C-shaped hook body 52 defining an opening 54 sized to receive the walker 16 therethrough. The C-shaped hook body 52 may include a locking arm 56 that is pivotally connected to the C-shaped hook body 52 for closing the opening 54 of the C-shaped hook body 52, and a biasing spring 58 for biasing the locking arm 56 from an open position wherein the opening 54 is open, to a closed position wherein the opening 54 is closed.

While the current embodiment includes clamps 20 and 50 of the illustrated constructions, alternative clamps, hooks, connectors, and equivalent devices known in the art may also be used, and such alternatives should be considered within the scope of the present invention.

Figure 7:
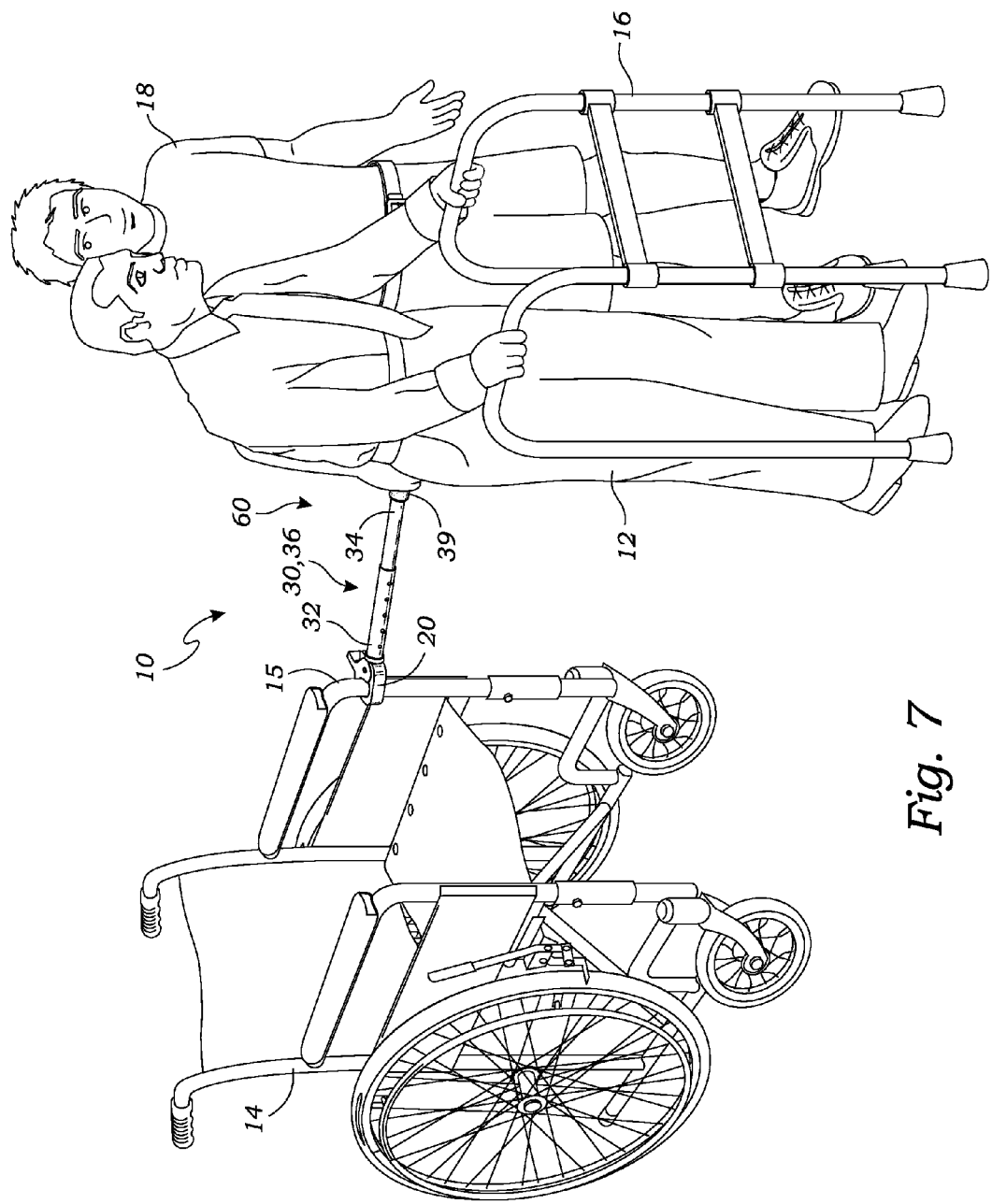
FIG. 7 is a perspective view of the gait training tool of FIG. 3, using the manual gripping attachment, operatively attached to a wheelchair and manually pulled by the caregiver during assisted gait training.

FIG. 7 is a perspective view of the gait training tool 10 of FIG. 3, using the manual gripping attachment 60, operatively attached to the wheelchair 14 and manually pulled by the caregiver 18 during assisted gait training. As shown in FIG. 7, the length of the gait training tool 10 is readily adjustable in this embodiment, to accommodate the needs of the users. The gait training tool 10 enables the caregiver 18 to remain positioned facing the patient 12, ready to assist him or her in the event of a problem, while easily pulling the wheelchair 14 as needed so that the wheelchair 14 is always readily available to the patient 12 if needed.

Figure 8:
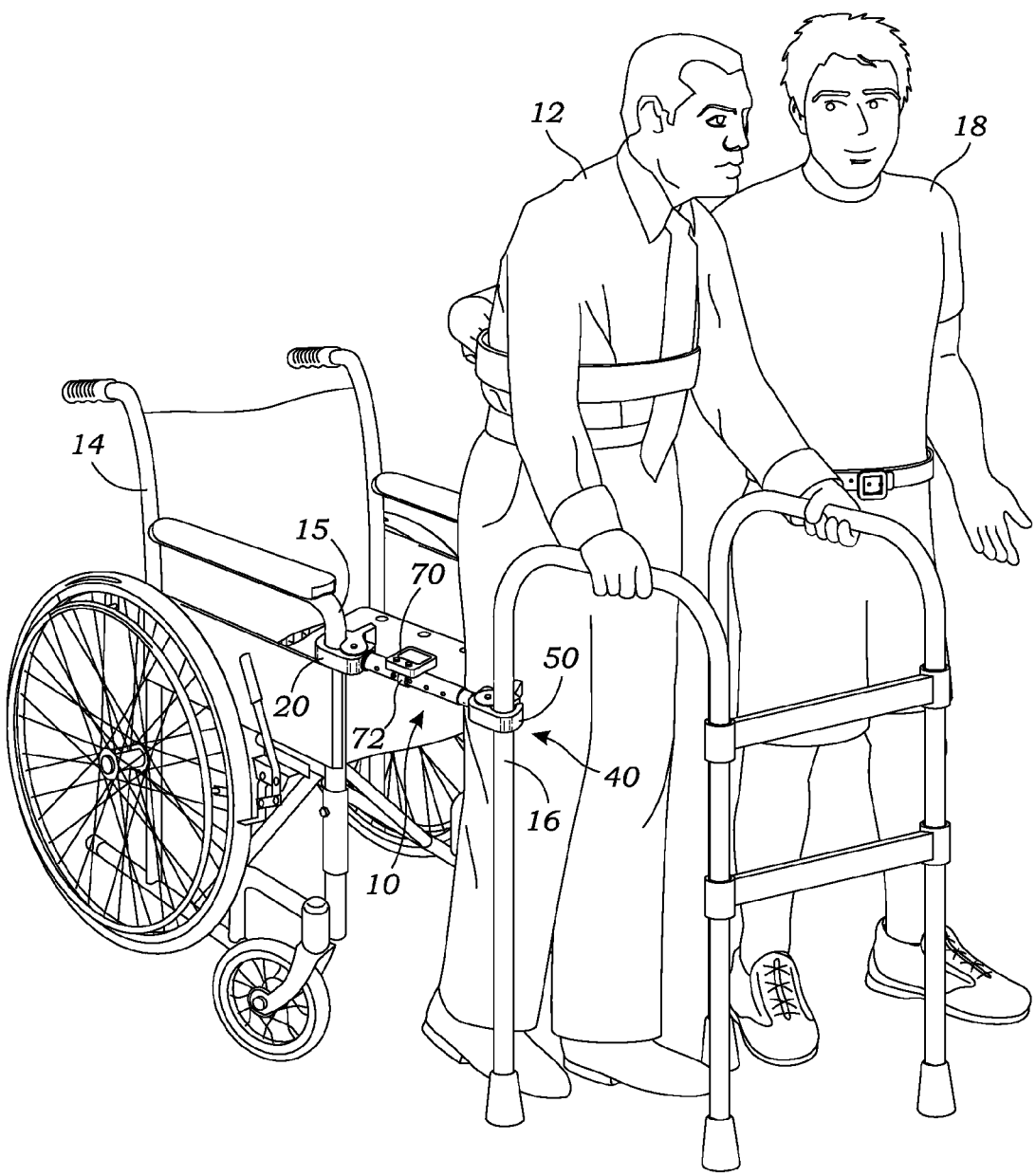
FIG. 8 is a perspective view of the gait training tool of FIG. 3, using the walker connection attachment, operatively attached to the wheelchair and to the walker while the caregiver performs assisted gait training, and further illustrating a gait tracking system.

FIG. 8 is a perspective view of the gait training tool 10 of FIG. 3, using the walker connection attachment 40, operatively attached to the wheelchair 14 and to the walker 16 while the caregiver 18 performs the assisted gait training. The gait training tool 10 is attached to both the wheelchair 14 and the walker 16, using the clamps 20 and 50, as described above, and the length of the gait training tool 10 may be adjusted, as discussed above. The caregiver 18 may assist the patient 12, as needed, in moving the walker 16 forward, and thereby also advancing the wheelchair 14. If the patient 12 becomes fatigued, he or she can readily sit in the wheelchair 14 to rest and recover. At all times, the caregiver 18 can remain in position to assist the patient 12, as needed.

Figure 9:
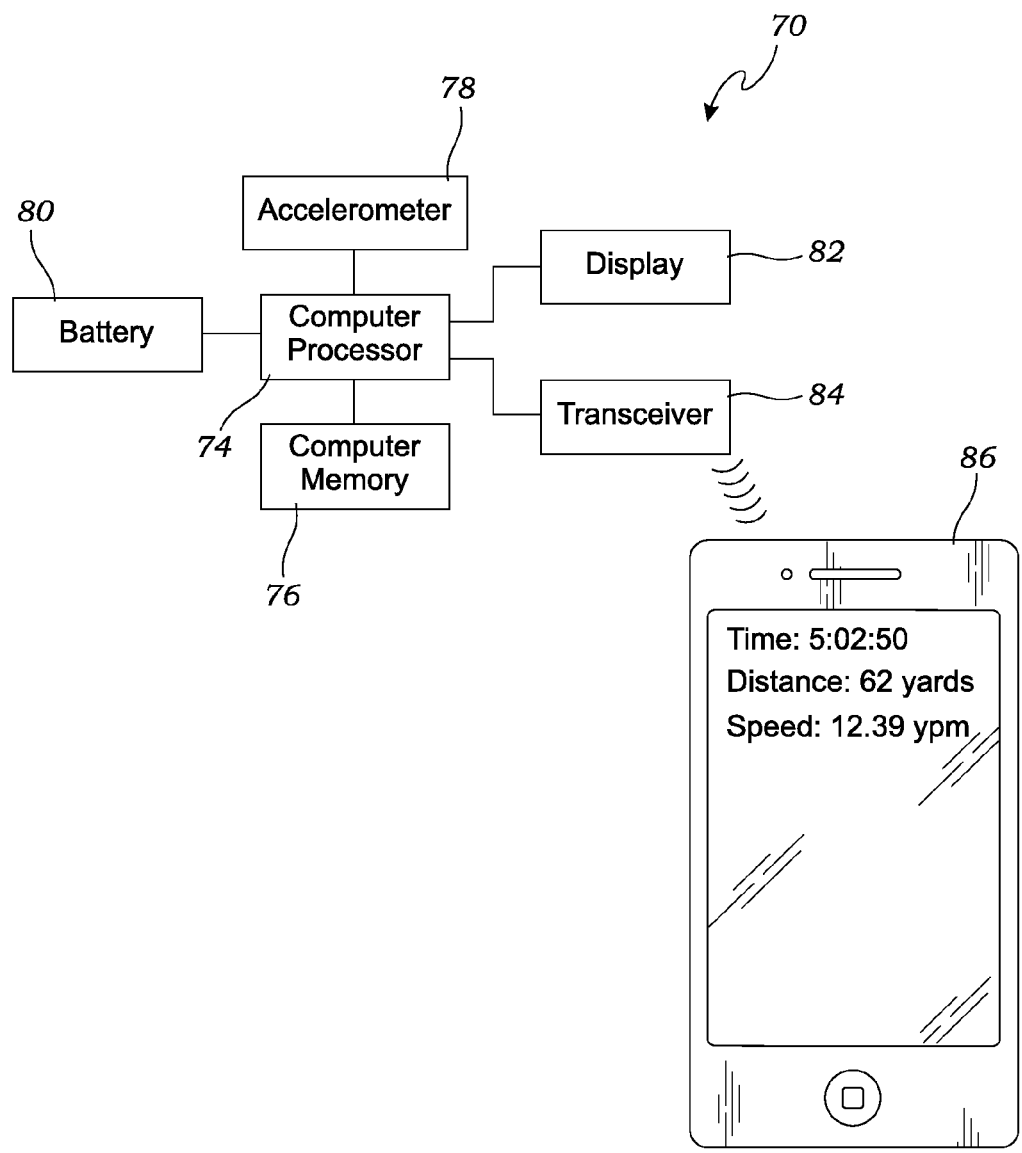
FIG. 9 is a block diagram of the gait tracking system of FIG. 8, which electronically tracks movement of the gait training tool, and reports the progress of the gait training.

As shown in FIG. 8, the gait training tool 10 may further include a gait tracking system 70 for electronically tracking the progress of the patient 12 using the gait training tool 10. The gait tracking system 70 is illustrated in FIG. 9, and discussed in greater detail below. The gait tracking system 70 is mounted on the gait training tool 10, such as with a mounting structure 72 (e.g., a strap, fasteners such as screws, special housing adapted for mounting the gait tracking system 70 on the gait training tool 10, etc.). The movement of the gait training tool 10 is then tracked via the gait tracking system 70.

FIG. 9 is a block diagram of the gait tracking system 70, shown in FIG. 8, that electronically tracks movement of the gait training tool 10, and reports the progress of the gait training. As shown in FIG. 9, in the present embodiment, the gait tracking system 70 comprises a computer processor 74, a computer memory 76, and an accelerometer 78 operably connected with the computer processor 74 for tracking movement of the gait tracking system 70.

As shown in FIG. 9, the gait tracking system 70 may include a battery 80 for powering the system, a display 82 for reporting the results of the tracking (e.g., time spent on gait training, distance traveled, average speed, etc.), and may further include a transceiver 84 for transmitting the results to a portable electronic device 86 (e.g., a smart phone, tablet, or any form of computer device that stores a patient's electronic records).

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A gait training tool for performing gait training of a patient using a wheelchair having a frame, the gait training tool comprising:
   an elongate frame structure having a proximal end and a distal end;
   a wheelchair clamp attached to the proximal end of the elongate frame structure;
   a walker connection attachment having a walker clamp and an engaging structure for removably engaging the walker connection attachment on the distal end of the elongate frame structure;
   a manual gripping attachment having a cylindrical gripping structure and an engaging structure for removably engaging the manual gripping attachment on the distal end of the elongate frame structure; and a computer processor; a computer memory; and
   an accelerometer operably connected with the computer processor for tracking movement of the gait tracking system.

2. The gait training tool of claim 1, wherein the elongate frame structure of the gait training tool includes a first frame element, and the engaging structures of the walker connection attachment and the manual gripping attachment include a second frame element, the first and second frame elements being shaped to slidably engaging each other so that the length of the elongate frame structure can be adjusted, the elongate frame structure further including a locking element that locks the first and second frame elements at a selected length.

3. The gait training tool of claim 2, wherein the first frame element and the second frame element are both elongate tubular structures, and the second frame element telescopically engages the first frame element.

4. The gait training tool of claim 3, wherein the locking element includes a locking pin that extends through an aperture of the second frame element and also through one of a plurality of openings of the first frame element, a spring of the locking pin biasing the locking pin outwardly through the one of the plurality of openings.

5. The gait training tool of claim 1, wherein the wheelchair clamp includes a C-shaped hook body that is shaped to fit around the frame of the wheelchair, the C-shaped hook body defining an opening sized to receive the frame of the wheelchair therethrough, a locking arm that is pivotally connected to the C-shaped hook body for closing the opening of the C-shaped hook body, and a biasing spring for biasing the locking arm from an open position wherein the opening is left open, to a closed position wherein the opening is closed.

6. The gait training tool of claim 1, wherein the walker attachment clamp has a C-shaped hook body that is shaped to fit around the walker, the C-shaped hook body defining an opening sized to receive the walker therethrough, a locking arm that is pivotally connected to the C-shaped hook body for closing the opening of the C-shaped hook body, and a biasing spring for biasing the locking arm from an open position wherein the opening is left open, to a closed position wherein the opening is closed.

7. The gait training tool of claim 1, wherein the cylindrical gripping structure is constructed of a foam rubber sleeve bonded over the distal end of the gait training tool.

8. The gait training tool of claim 1, wherein the walker attachment clamp has a C-shaped hook body that is shaped to fit around the walker, the C-shaped hook body defining an opening sized to receive the walker therethrough, a locking arm that is pivotally connected to the C-shaped hook body for closing the opening of the C-shaped hook body, and a biasing spring for biasing the locking arm from an open position wherein the opening is left open, to a closed position wherein the opening is closed.

9. A gait training tool for performing gait training of a patient using a wheelchair having a frame, the gait training tool comprising:
   an elongate frame structure having a proximal end and a distal end;
   a wheelchair clamp attached to the proximal end of the elongate frame structure;
   a walker connection attachment having a walker clamp and an engaging structure for removably engaging the walker connection attachment on the distal end of the elongate frame structure;
   a manual gripping attachment having a cylindrical gripping structure and an engaging structure for removably engaging the manual gripping attachment on the distal end of the elongate frame structure;
   wherein the elongate frame structure of the gait training tool includes a first frame element, and the engaging structures of the walker connection attachment and the manual gripping attachment each include a second frame element, and wherein the first and second frame elements slidably engaging each other so that the length of the elongate frame structure can be adjusted;

a locking element that locks the first and second frame elements; and a computer processor; a computer memory; and an accelerometer operably connected with the computer processor for tracking movement of the gait tracking system.

10. The gait training tool of claim 9, wherein the walker attachment clamp has a C-shaped hook body that is shaped to fit around the walker, the C-shaped hook body defining an opening sized to receive the walker therethrough, a locking arm that is pivotally connected to the C-shaped hook body for closing the opening of the C-shaped hook body, and a biasing spring for biasing the locking arm from an open position wherein the opening is left open, to a closed position wherein the opening is closed.

11. The gait training tool of claim 9, wherein the first frame element and the second frame element are both elongate tubular structures, and the second frame element telescopically engages the first frame element.

12. The gait training tool of claim 9, wherein the locking element includes a locking pin that extends through an aperture of the second frame element and also through one of a plurality of openings of the first frame element, a spring of the locking pin biasing the locking pin outwardly through the one of the plurality of openings.

* * * * *